US010893957B2

(12) United States Patent
Glasgow

(10) Patent No.: US 10,893,957 B2
(45) Date of Patent: *Jan. 19, 2021

(54) MECHANICAL GRASPING DEVICE

(71) Applicant: Ryan William Glasgow, Portland, OR (US)

(72) Inventor: Ryan William Glasgow, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,335

(22) Filed: May 3, 2018

(65) Prior Publication Data

US 2018/0250146 A1    Sep. 6, 2018

Related U.S. Application Data

(62) Division of application No. 15/072,281, filed on Mar. 16, 2016, now Pat. No. 10,271,966.

(51) Int. Cl.
| | | |
|---|---|---|
| *A61F 2/58* | (2006.01) | |
| *A61F 2/68* | (2006.01) | |
| *A61F 2/50* | (2006.01) | |
| *A61F 2/70* | (2006.01) | |

(52) U.S. Cl.
CPC .............. *A61F 2/583* (2013.01); *A61F 2/586* (2013.01); *A61F 2002/502* (2013.01); *A61F 2002/5003* (2013.01); *A61F 2002/5009* (2013.01); *A61F 2002/5018* (2013.01); *A61F 2002/5073* (2013.01); *A61F 2002/5093* (2013.01); *A61F 2002/587* (2013.01); *A61F 2002/6854* (2013.01); *A61F 2002/701* (2013.01)

(58) Field of Classification Search
CPC .. A61F 2/583; A61F 2/586; A61F 2002/5093; A61F 2002/587; A61B 34/70–71
USPC ......................................... 901/30–32, 35–39
See application file for complete search history.

(56) References Cited

U.S. PATENT DOCUMENTS

| | | | | |
|---|---|---|---|---|
| 3,694,021 A | * | 9/1972 | Mullen .................... | A61F 2/583 294/106 |
| 5,280,981 A | * | 1/1994 | Schulz ................... | B25J 15/103 294/106 |
| 5,762,390 A | * | 6/1998 | Gosselin ................ | B25J 15/103 294/106 |
| 9,814,604 B2 | * | 11/2017 | Jury ........................ | A61F 2/583 |

(Continued)

*Primary Examiner* — Marcia L Watkins
(74) *Attorney, Agent, or Firm* — Mark S Hubert

(57) ABSTRACT

A mechanical grasping device where each of the segments of the finger assemblies, are individually sizeable. This allows for both a proportionately scalable grasping device as well as individual customization of geometric configurations tailored to specific use patterns. The mechanical grasping device is crushable since it has flexible and pivotable connections between digits along its length and width. It has a hollow member construction that imparts a strong lightweight design. It is modular so individual parts can be replaced for quick repair. From an aesthetics point, it is visually pleasing and can be offered in different colors, and with custom digit sleeves for specific applications. Finger assemblies can be operated individually or in groups via pairs of cables which allow operation in either voluntary open or voluntary closed modes of control. The flexible construction allows gripping of irregularly shaped objects and deforms before failing giving indication of overload prior to failure.

8 Claims, 22 Drawing Sheets

(56) References Cited

U.S. PATENT DOCUMENTS

| | | | |
|---|---|---|---|
| 10,271,966 B2* | 4/2019 | Glasgow | A61F 2/583 |
| 2010/0156125 A1* | 6/2010 | Lee | B25J 15/0009 |
| | | | 294/192 |
| 2013/0057004 A1* | 3/2013 | Murata | B25J 15/0009 |
| | | | 294/106 |
| 2016/0367383 A1* | 12/2016 | Sensinger | A61F 2/583 |

* cited by examiner

MECHANICAL GRASPING DEVICE

PRIORITY

This utility patent application is a Divisional Patent Application claiming priority to and incorporating by reference U.S. patent Ser. No. 15/072,281 filed 2016 Mar. 16, now U.S. Pat. No. 10,271,966 issued Apr. 30, 2019, entitled "Improved Mechanical Prosthetic Hand."

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

The present invention relates to a novel design for a mechanical grasping device more specifically described as a mechanical hand that introduces a new level of tactile operation for those who need such prosthetic devices. It is adapted to matingly connect with various standardized prosthetic hand/arm components, thereby allowing a simple conversion for existing prosthetic hand users, although the design elements herein may be incorporated in various styles of mechanical grasping devices.

BACKGROUND OF THE INVENTION

Despite the portrayal of high tech prosthetic hands as the norm on the media, the current state of the art for prosthetic hands/arms for the average person leaves much to be desired. The most widely used terminal device is known as the "Hosmer™ Hook" and has been around since 1912. The basic Hosmer™ Hook has a single pair of opposable, crescent shaped pinchers. It is a voluntary-open terminal device having a series of elastic bands that keep the pinchers closed. It is body-powered, very reliable, predictable, waterproof, affordable and enables precise grasping of small objects with good visibility of item being grasped. It is very robust and capable of manipulations with very small items. Unfortunately, it has several drawbacks. It is somewhat menacing to look at, visually intimidating to third parties, has a limited ability to grasp irregularly shaped or large objects, does not lend itself to disguise with garment cover. While this device performs a single pinching task well, it is limited to manipulations from rigid, non-adjustable, fixed length pinchers rotating in a single plane.

Other more sophisticated (e.g. robotic) hands are capable of performing with more dexterity but are also limited in many ways. These five-fingered robotic hands tend to feature complex electro-mechanical assemblies and as such tend to be expensive, fragile and require a silicone glove to be waterproof. They are non flexible, non customizable and frequently incorporate motors or other electrical systems within the hand itself resulting in a stiff monolithic palm which is not scalable and not lifelike. Performance of these hands is limited by battery life. Many of such prosthetic hands are not scalable or available in small sizes for children or women.

Henceforth, an aesthetically appealing, body-powered, five-fingered, prosthetic hand, would fulfill a long-felt need in the prosthetic device industry. Similarly, a scalable prosthetic hand that replicated the dynamic flexibility of a human hand would allow for greater utility, as well as improved visual and emotional acceptance. Finally, a mechanical grasping device that is a subsection of the prosthetic hand would offer numerous advantages over the prior art. This new invention utilizes and combines known and new technologies in a unique and novel configuration to overcome the aforementioned problems and accomplish this.

SUMMARY OF THE INVENTION

In accordance with the invention, the object of the present invention, which will be described subsequently in greater detail, is to provide an improved mechanical hand that is able to connect to a user's existing body-powered harness or myoelectric controlled systems.

It is another object of the present invention to provide a prosthetic hand that approximates the look and function of the human hand with five digits capable of being manipulated with an opposable thumb capable of adjustable angle opposability.

It is yet another object of the present invention to make a human hand-like prosthetic device wherein each digit is made from a series of different sized connected elements so as to allow scalability of the device.

It is still another object of the present invention to provide a lightweight prosthetic hand that can be fabricated from the assembly of a minimal number of components, many identical, each of which can be economically and simply fabricated.

It is a further object of the present invention to provide a prosthetic hand with the capacity for individual digit control.

It is still another object of the present invention to offer a prosthetic hand that has set of digits that incorporate metacarpal members which pivot at their proximal end in a plane that resides approximately 90 degrees relative to the plane of curl or extension of the digits.

It is another object of the present invention to offer an improved, robust prosthetic hand capable of providing an entire host of different grasping and holding features configured similar to a human hand so as to present a five-digit crushable compliant grasping profile that is able to be powered/operated by a industry standard body powered harness.

It is a final object of the present invention to offer an abbreviated mechanical hand, one that is made with a subset of the components of the prosthetic hand, that can be used in simpler, less demanding situations as a mechanical grasping device.

The improved mechanical/prosthetic hand has many of the advantages mentioned heretofore and many novel features that result in a grasping device capable of use as a new human hand-like device or a mechanical grasping device which is not anticipated, rendered obvious, suggested, or even implied by any of the prior art, either alone or in any combination thereof.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

BRIEF DESCRIPTION OF THE DRAWINGS

Note: Only FIGS. 5 and 10 show the operational cables. The operational cables have otherwise been removed for diagrammatic simplification and visual clarity. (While the term 'cables' shall be used henceforth, it is understood that any type of tensile member can be used, (eg, string or rope.) Only FIGS. 1, 2, 3, 4 and 18 show the flexible spacers. The flexible spacers have otherwise been removed from FIGS. 3, 4, 16, 17 and 19-21 for diagrammatic simplification and visual clarity.

DETAILED DESCRIPTION

Figure 1:
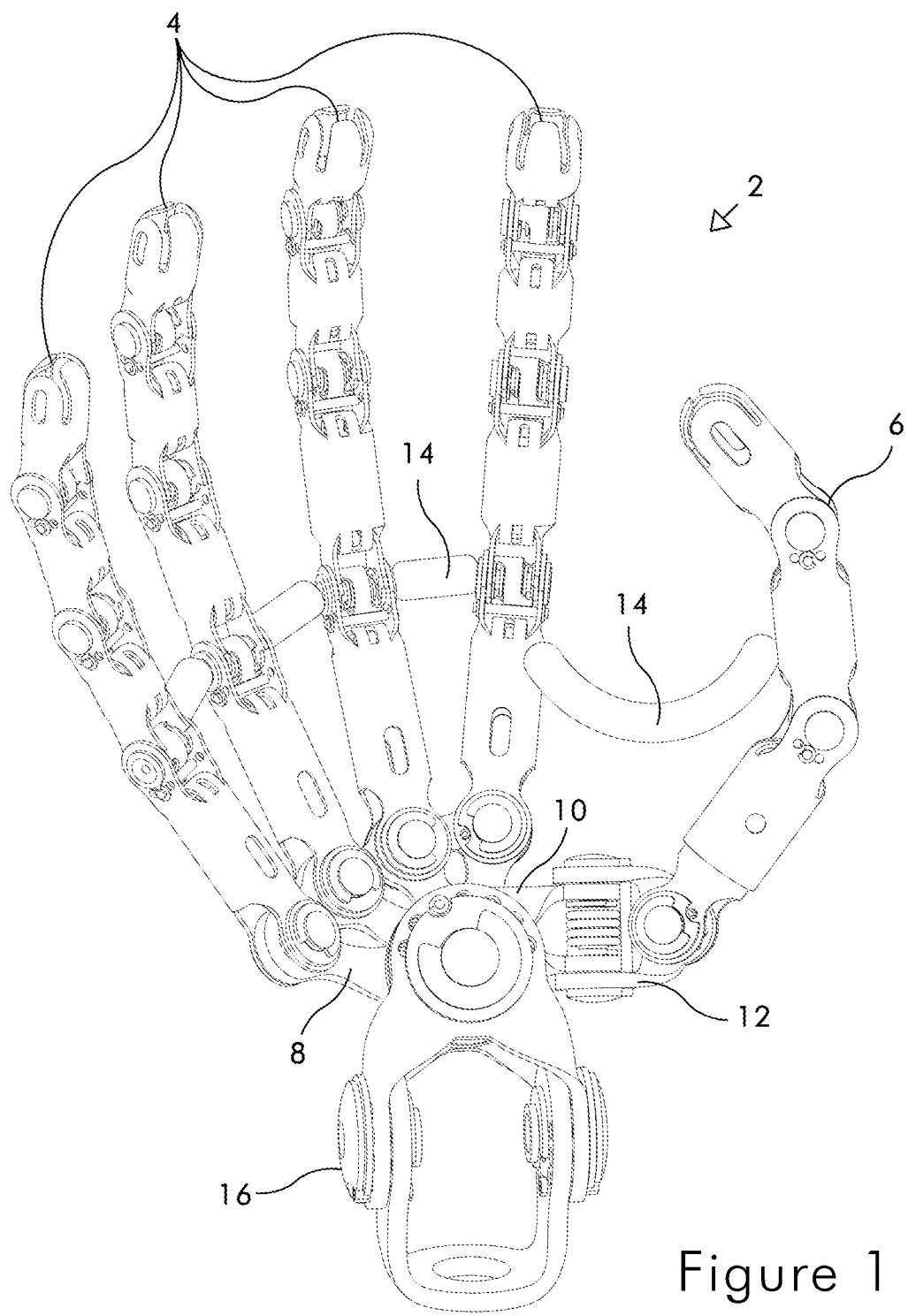
FIG. 1 is a front perspective view of the prosthetic hand with attached flexible spacers.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. As an exemplar, the number of digits and type of digit and scalable size of each digit is fully customizable for both prosthetic and robotic applications. Also, it is to be understood that the phraseology and terminology employed herein are for the purpose of descriptions and should not be regarded as limiting.

As used herein, the term "mechanical hand" or "prosthetic hand" refers to a device often referred to as a mechanical arm or prosthetic arm. The most basic structure is referred to as a mechanical grasping device. Although discussed herein used as a prosthetic hand, it is known that it may also be used as a grasping device with applications as prosthetics as well as in robotics or other powered applications as well because of its human hand-like tactile similarities.

When fashioned as a human hand, the grasping device has four digits that approximate fingers having four separately scalable elements pivotally connected in a linear fashion from a distal phalange at the tip, a middle phalange, a proximal phalange and lastly a metacarpus, as well as a fifth digit that approximates a thumb and resembles the other digits but lacks a middle phalange. These are connected to a support member.

When fashioned as a mechanical grasping device for other than aesthetically pleasing human hands, it is a simplified version of the prosthetic hand and has at least two digits (now called finger assemblies) made of at least two separately scalable elements (now called digit segments) pivotally connected to a support member. The difference in nomenclature is for distinction between the prosthetic hand and the basic mechanical grasping device. The mechanical grasping device may be used as a human prosthetic although it is more likely to be used in robotics.

The term "crushable" refers to the ability to have the digits of the mechanical hand or the mechanical grasping device simultaneously pivot at their proximal connections to the palmer plate (support member) and also simultaneously flex slightly about their polymer spacers when external forces are applied. In this manner, the digits (finger assemblies) may be forced together or undergo individual shocks without damage to the hand.

It is to be noted, that because of the similarities between the prosthetic hand and the human hand, much of the medical terminology of the human hand has been adopted for the designations of the various elements of the device.

The improved prosthetic hand 2 has been modeled after the human form with five scalable digits. Each digit is separately capable of dorsal extension (finger opening) and palmar flexion (finger closing) and with the ability to be individually controlled as desired.

Figure 2:
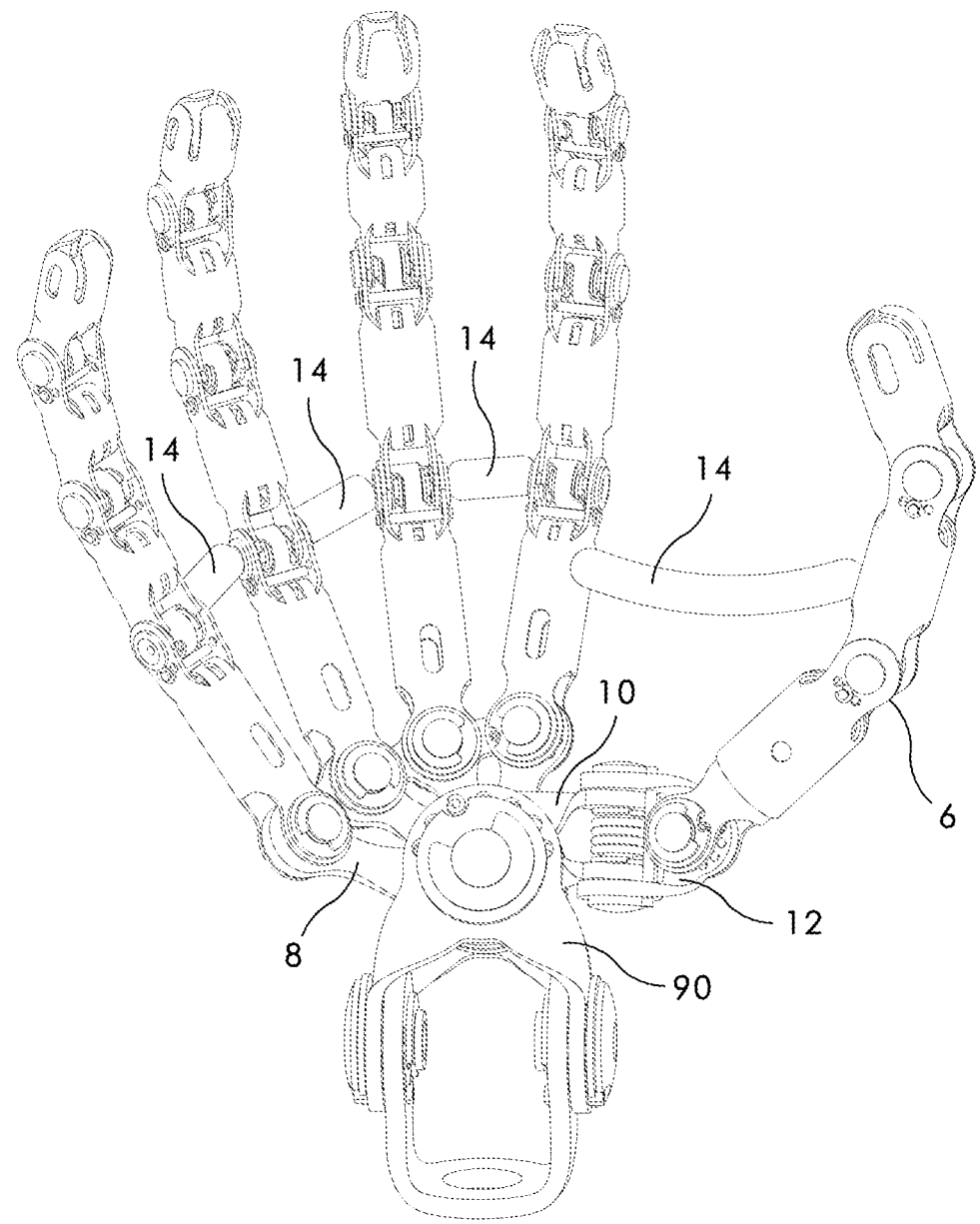
FIG. 2 is a front perspective view of the prosthetic hand with attached flexible spacers and thumb.

Looking at FIGS. 1 and 2, it can be seen that the hand 2 has seven parts: the finger digits 4; the thumb digit 6; the palmar plate 8; the thumb rotation plate 10; the thumb pivot flange 12; the flexible spacers 14; and the wrist 16.

The mechanical grasping device 100 (FIG. 22) in contrast, is simplified and need not have a thumb but rather just at least two finger assemblies 104 pivotally connected to a support member 106. The finger assemblies need only be made of two hingeable digit segments.

The palmar plate 8 is the central hub or means for operationally supporting all of the digits or digital movements. It also mounts to the wrist for operational connection to the user. In the mechanical grasping device embodiment, the palmar plate 8 is referred to as a support member and the proximal end of the finger assemblies is pivotally affixed thereto.

The hand 2 is designed to be a terminal device wherein it is affixed to a standard prosthetic socket that mounts to the distal end of the user's residual limb. Generally, a socket is fitted on the residual limb and connects the residual limb to the prosthetic device 2. These sockets are attached by a tight, custom friction or vacuum fit over the residual limb. The connection of the prosthetic hand 2 to the residual limb is not discussed herein. There are several different matingly engageable mechanical configurations that may be utilized, each of which is commercially available. Adaption of the prosthetic hand to any of these devices is merely an act of mechanical manipulation as would be well known by one skilled in the art.

Figure 20:
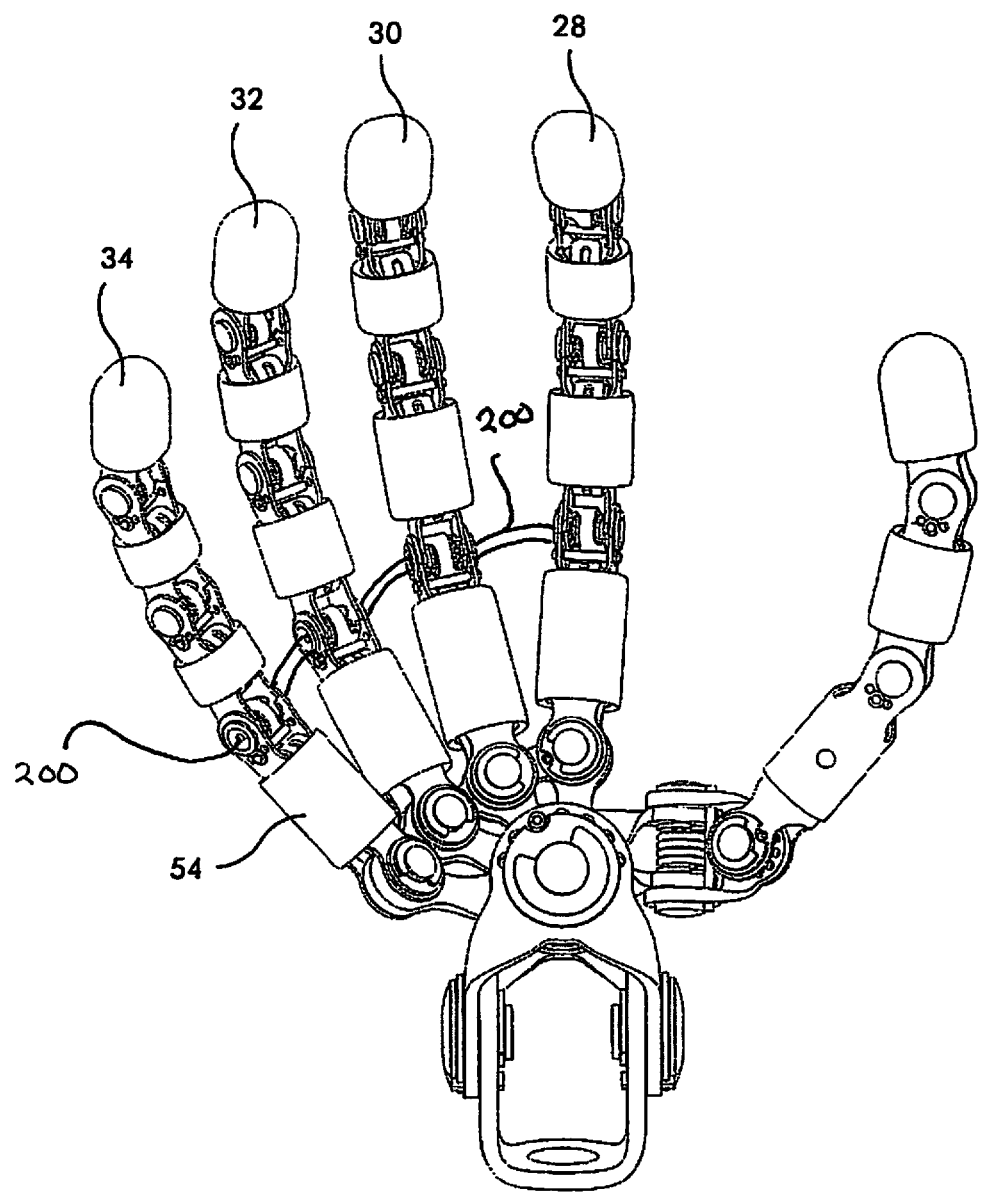
Figure 21:
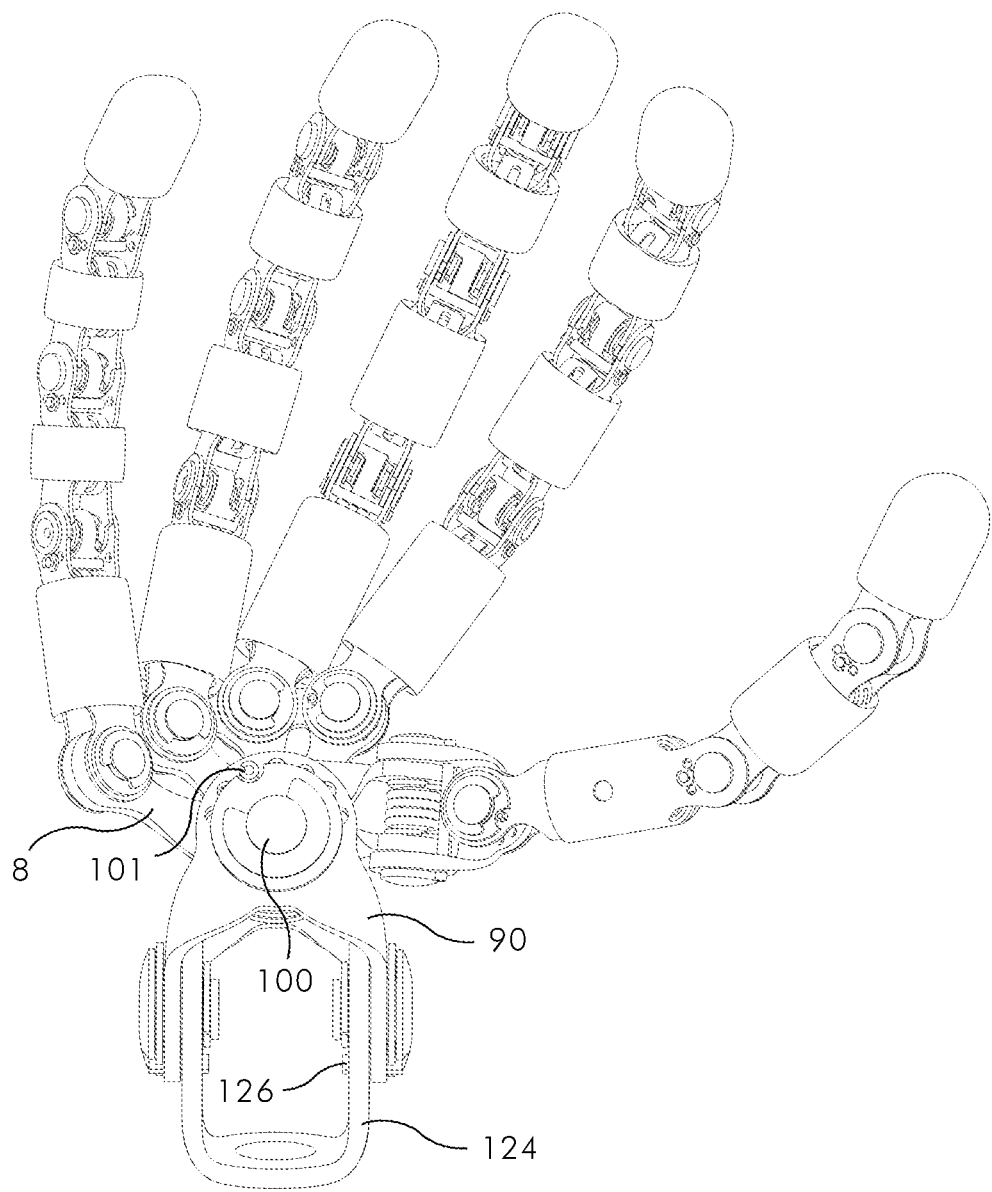

Operation of the prosthetic hand may be via one of the common cable and sling arrangements that are typically worn up the arm and across the shoulders of the user (body powered). Optionally, the prosthetic hand 2 may be operated by motorized driven myoelectric control initiated by a signal. Such signals may come from an electrical impulse generated by an electrode operationally contacting a muscle group. (e.g. in the forearm) It is to be noted that whether used as a human prosthetic device, or as a mechanical grasping device, it is designed to be crushable, having flexible spacers 14 between all adjacent digits (finger assemblies) along the width of the hand 2, as well as pivotal connections at the base of each finger digit 4 (finger assembly) and the thumb digit 6. These flexible spacers 14 in the preferred embodiment are simply flexible cables 200 sheathed with a pliable polymer between the sections spanning adjacent digits (finger assemblies). (See FIGS. 4 and 20) There are flexible spacers 14 spanning between adjacent digits (finger assemblies) in the prosthetic hand 2, between the pinky digit 34 and index digit 28. The flexible cables 200 with the pliable polymer sheath removed can better be seen in FIG. 20.

There is another one spanning between the index digit 28 and the thumb digit 6. (Although there may be more of less flexible spacers 14 to accomplish the same functionality of the hand 2.) This synergistic design allows for the "crushable" feature of the hand 2 and prevents irreparable harm to the hand or its components under unexpected mechanical loads or shock. Additionally, the flexible spacers 14 between all digits (finger assemblies) along the width of the hand 2, allows simultaneous limited motion of some or all of the digits (finger assemblies) with respect to the other digits (finger assemblies).

The prosthetic hand 2 has numerous physical configurations so that it can be individually customized for each user or for specific tasks that the user may be attempting. One such example can be seen in FIGS. 3 and 4 where it can be seen that the thumb digit 6 utilizes a tube-in-tube sleeved configuration that allows the adjustable, mechanical fixation of the thumb digit through a full range of rotations, as will be discussed in detail herein.

Figure 4:
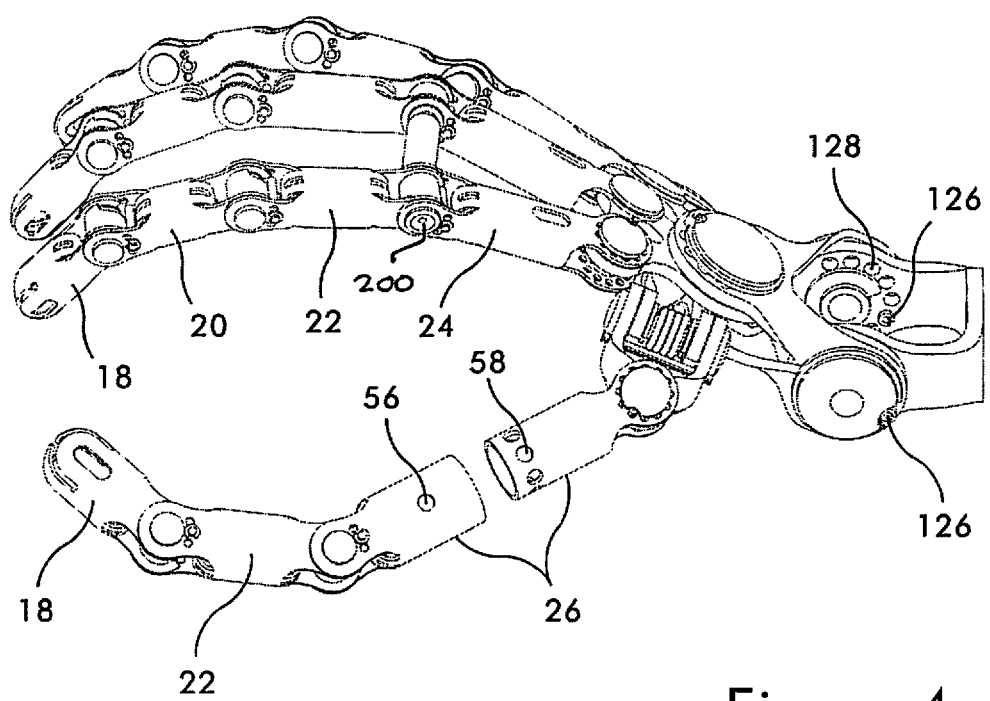
FIG. 4 is a side perspective of the prosthetic hand.
Figure 5:
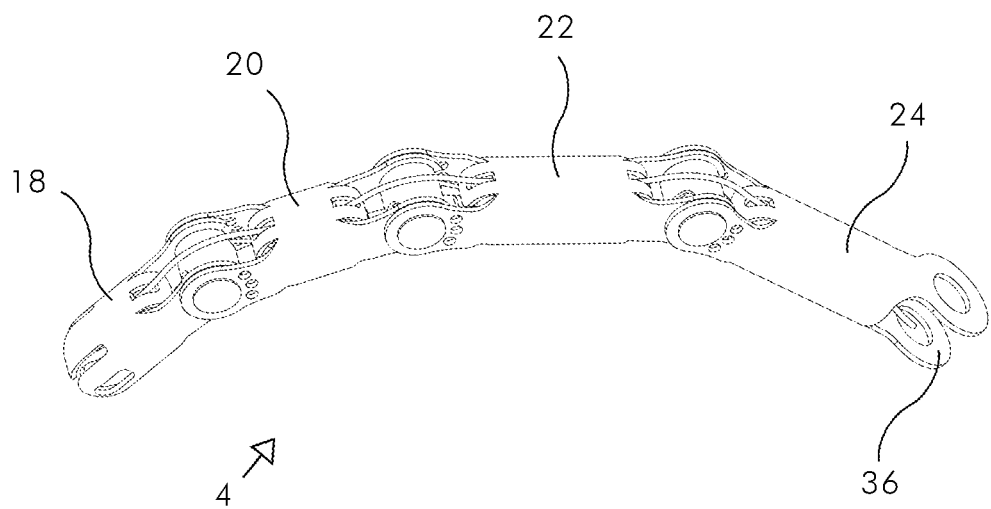
FIG. 5 is a top perspective view of a bent finger digit.
Figure 6:
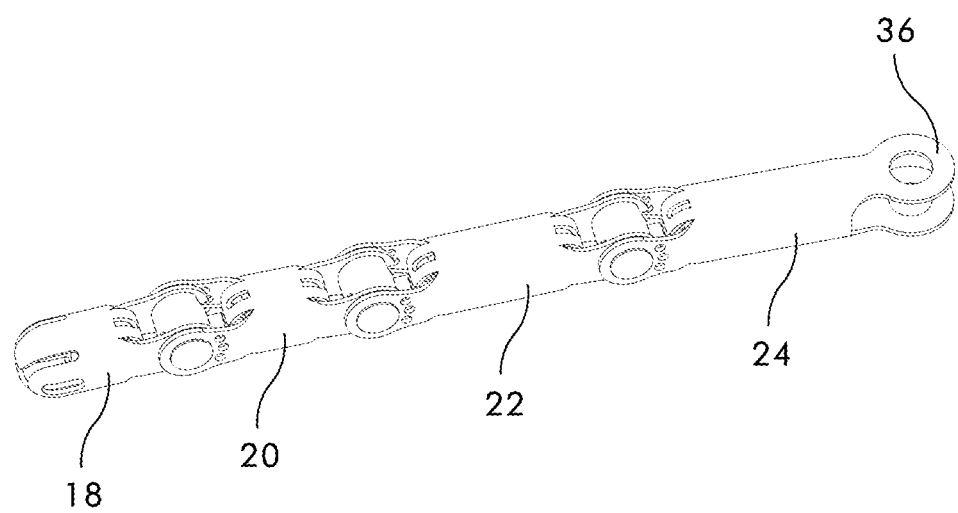
FIG. 6 is a side perspective view of a straightened finger digit.

Looking at FIGS. 4-6 it can be seen that four of the digits approximate fingers (finger digits 4) and have four separately scalable elements pivotally connected in a linear (series) fashion from a distal phalange 18 at the tip, a middle phalange 20, a proximal phalange 22 and lastly a metacarpus 24. The fifth digit approximates a thumb (thumb digit 6) and resembles the other digits but lacks a middle phalange 20 and has an axially adjustable metacarpus 26. Except for the elimination of the middle phalange 20 in the thumb digit 6 and the axially adjustable thumb digit metacarpus 26, the finger digit 4 and thumb digit 6 structures are functionally identical. Generally, the thumb digit 6 is the shortest of the digits. Each of the digits is capable of independent curling or straightening. Again, it is noteworthy to state that the length, width and thickness of the individual digits is variable as well as the number of phalanges used to construct the digits. (The ability of curling or straightening of the finger digits, in addition to their ability to pivot at the proximal end of their metacarpals in a plane that lies approximately 90 degrees relative to the plane of curl or extension of the digits, is one of the distinguishing and novel features of this hand/grasping device.)

From the thumb digit, outward the digits are index 28, middle 30, ring 32 and pinky 34. FIG. 5 shows a single digit or in the case of the mechanical grasping device, a finger assembly, although not all finger assemblies need be made of four digit segments. The proximal phalange 22 of the thumb digit 6 is connected to the index finger at its metacarpus by a flexible spacer 14. In the preferred embodiment, this spacer 14 is made of a cable held in a spring like fashion by a flexible polymer covering. This acts like the human hand's adductor pollicis and flexor pollicis brevis muscles to flexibly span the space between the thumb digit and finger digit, passively drawing the thumb to the palm without input from the control cables.

The proximal ends of each of the finger digits (or finger assemblies) terminates in a parallel pair of generally planar, substantially similar palm flanges 36. These palm flanges 36 lie in a plane that is generally perpendicular to the plane in which the digits (or digit segments) are hinged for curl and have a connector orifice formed therethrough. Generally, this is also true of the thumb digit 6 however, as discussed earlier, the thumb has an axially adjustable metacarpus 26. These palm flanges 36 are what connect the digits to the palmar plate 8 (or support member) and because of their perpendicular orientation with respect to plane of the finger curl, allow the metacarpals 24 and 26 of the digits to pivot in the same plane of the palmar plate 8 so as to allow the digits (finger assemblies) to adjust their proximity to adjacent digits (finger assemblies) and to move laterally, thereby imitating human fingers and allowing overall crushability of the hand 2 (mechanical grasping device). The degree lateral flexibility of the digits (finger assemblies) and overall crushability of the hand 2 can be controlled, in part, by varying the stiffness of the flexible spacers 14. It should also be noted that the flexible spacers 14 are individually connected to adjacent digits (finger assemblies), linking said digits in a web-like fashion, thus providing connectivity of the system as a whole, while retaining the desired flexible properties of the hand 2.

Figure 7:
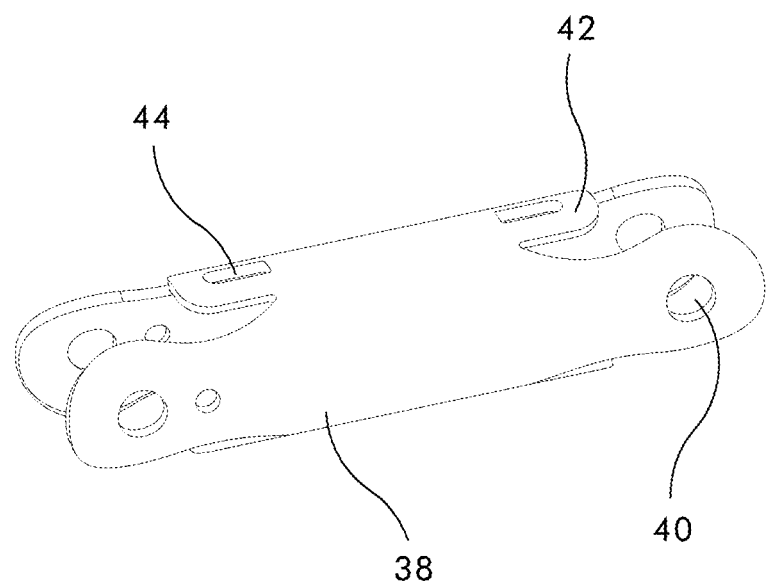
FIG. 7 is a side perspective view of a straight phalanges tube.
Figure 8:
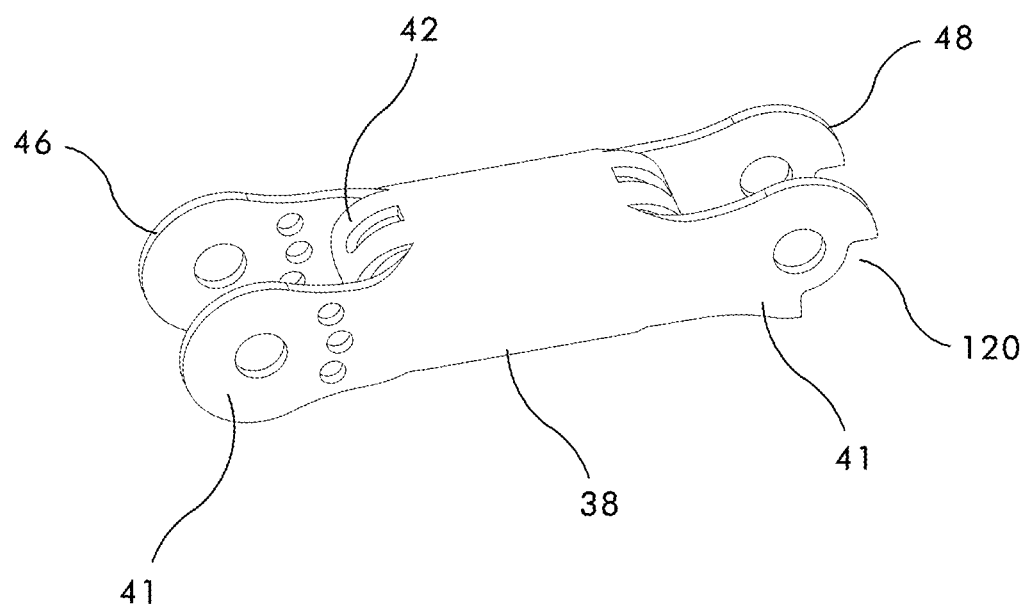
FIG. 8 is a side perspective view of a bent phalanges tube.
Figure 9:
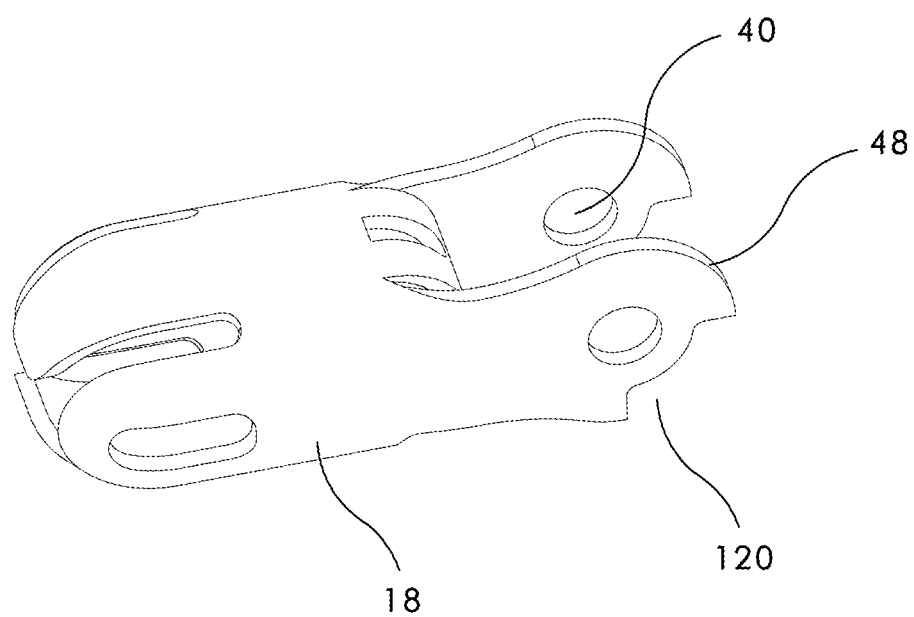
FIG. 9 is a side perspective view of a distal phalanges tube.

FIGS. 7-9 illustrate the most important individual component of the digits—that of the digit tube sections (digit segments). Each of the phalanges and metacarpals are made from a short tube section 38 cut or stamped and formed, or 3-D printed to a specific configuration. FIG. 7 shows the first stage of the construction of a tube section 38. The phalanges and metacarpals need not be formed from the same diameter tubing. In one embodiment the tubing is oval or circular, thin walled (0.030 in outer diameter wall thickness in the preferred embodiment) having a ½ inch outer diameter finger digits 4 and the distal end of the thumb digit metacarpal and a ⅝ outside diameter for the proximal end of the thumb digit metacarpal. Each end (distal or proximal) of the tube section 38 has a pair of opposing pivot pin orifices 40 formed there through at 180 degrees apart. Between the pair of pivot pin orifices 40, there resides a pair of opposing cable guides 42 formed by the absence/removal of tube wall sections there between the pivot pin orifices 40. Since the cable guides 42 terminate before the ends of the tube section, the distal and proximal ends of the tubes have parallel, opposing coupling flanges 41, through the center of which are the pivot pin orifices 40. It is these coupling flanges 41 that allow the relative motion of adjacent tube sections (digit segments). Each opposing cable guide 42 has a cable slot 44 there through and is much shorter than the coupling flanges 41. The coupling flanges 41 all reside generally parallel to the same plane except those at the proximal end of the metacarpus, which are perpendicular to the other coupling flanges.

FIG. 8 shows the second stage of construction where it can be seen that the ends of the four cable guides 42 are bent in an arc toward the longitudinal centerline of the tube section 38. Additionally, the distal end 46 and proximal end 48 of the tube section 38 are bend inward toward the tube section's center in a planar fashion about an axial planar bend line about the tube section 38 that also defines the beginning of the bend of the cable guides 42.

Figure 17:
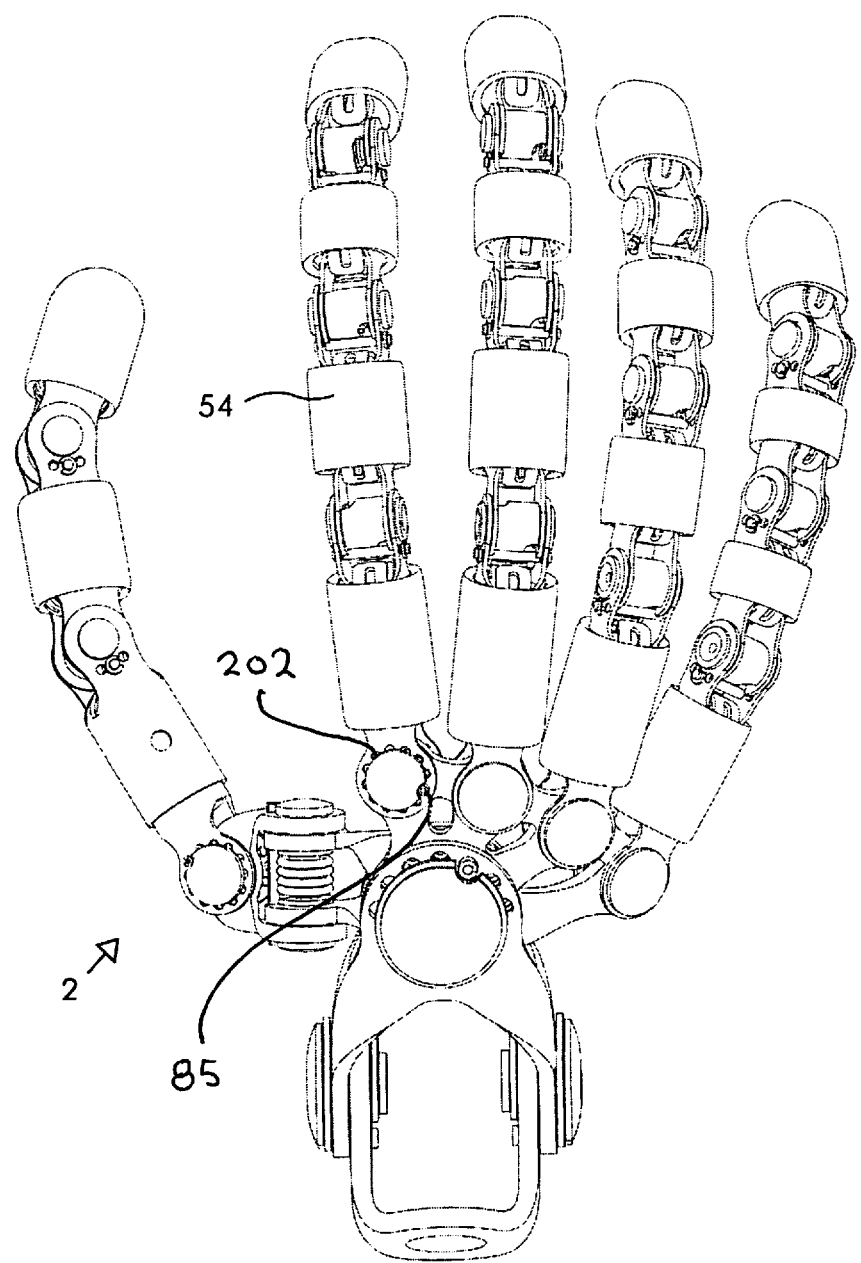
FIGS. 17-21 are front and rear perspective views of the prosthetic hand showing various finger, thumb and palm positions.
Figure 18:
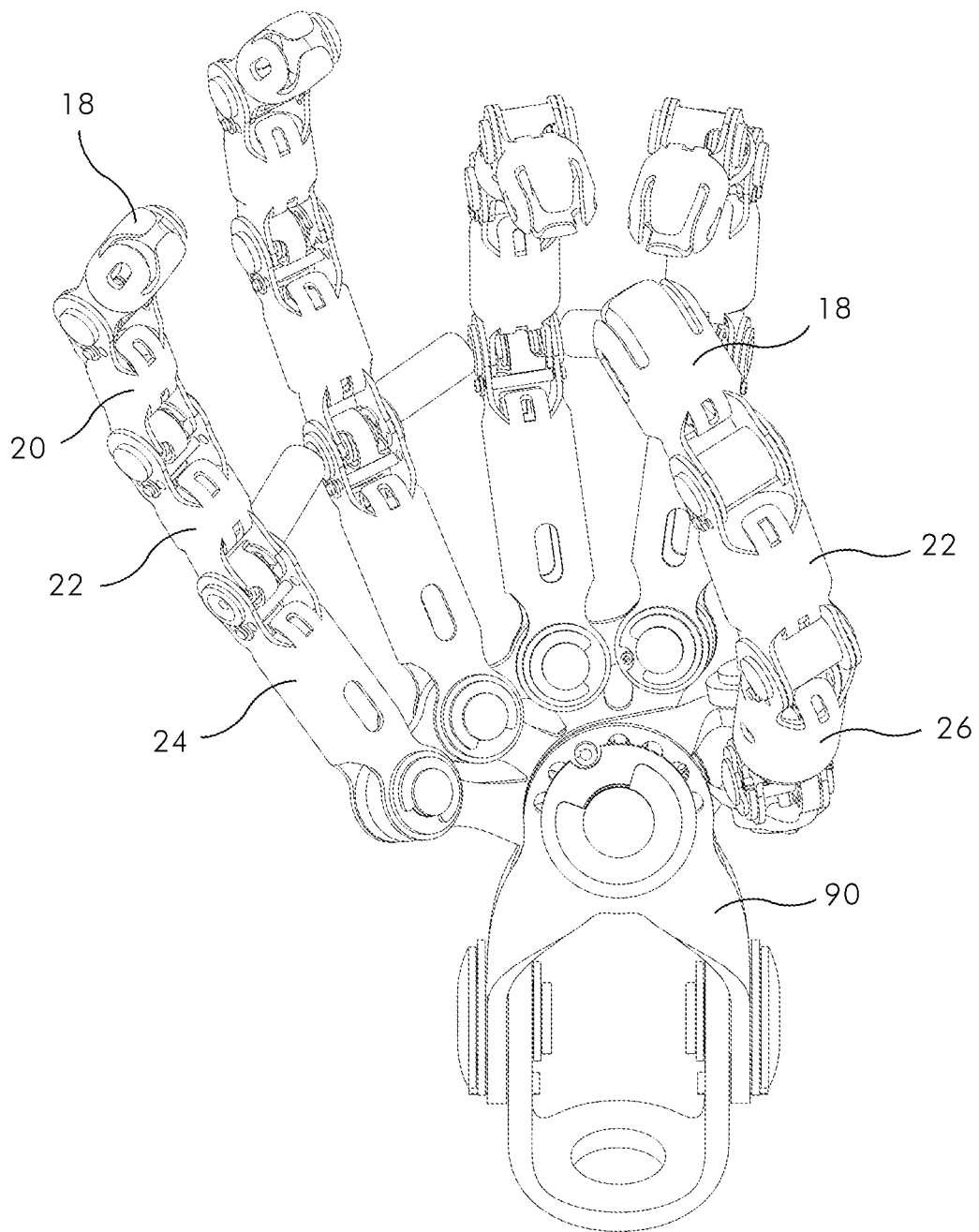
Figure 19:
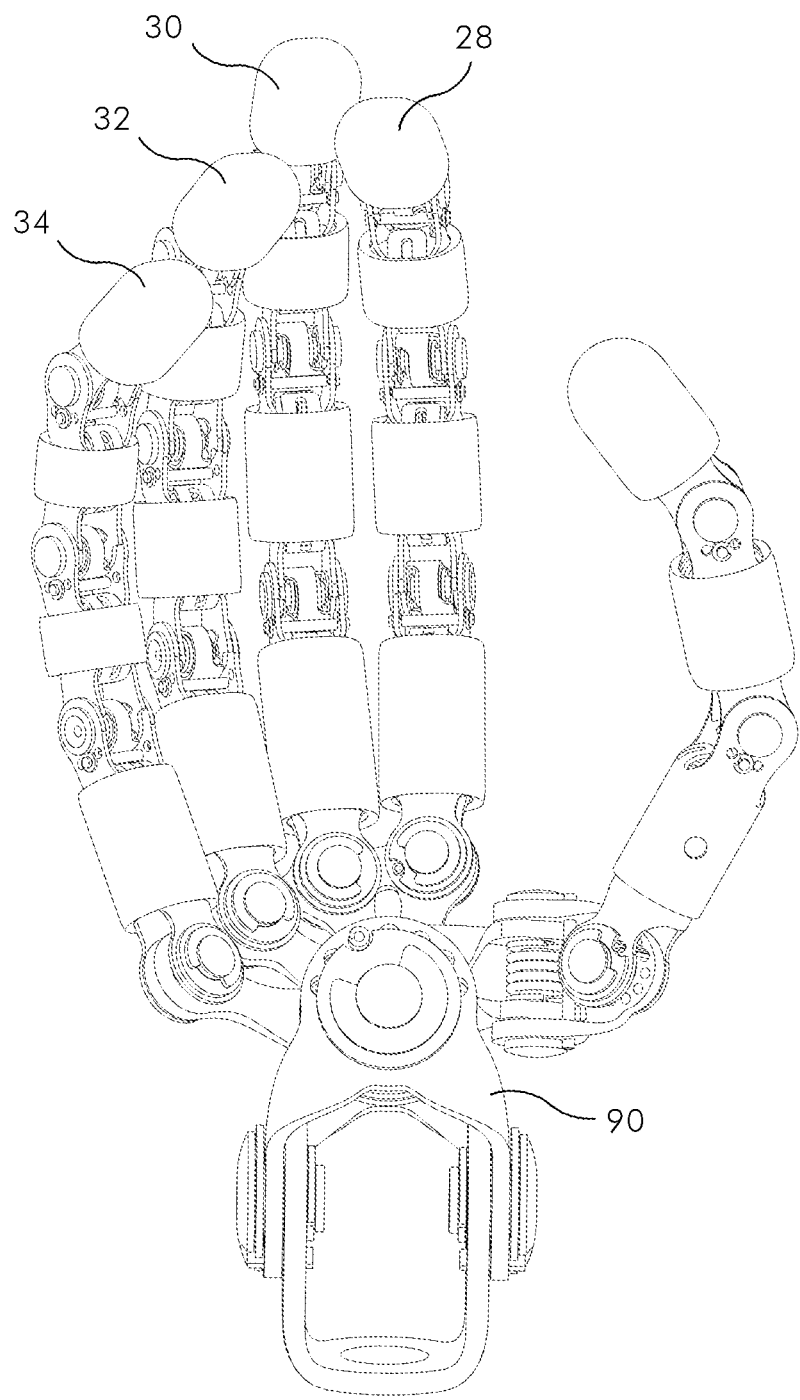

Looking at FIGS. 5 and 6 it can be seen that the distal phalange 18 differs from the middle phalange 20, and proximal phalange 22 because its distal and proximal ends are not identical. Rather, at the distal end, the entire distal end of the tube is bent towards the tube's longitudinal centerline so as to approximate the shape of a fingertip. An optional fingernail may be affixed to this phalange. Similarly, an optional polymer sleeve 54 (FIG. 17) may be placed about the center of the tube sections 38 for aesthetics and functional reasons.

Figure 16:
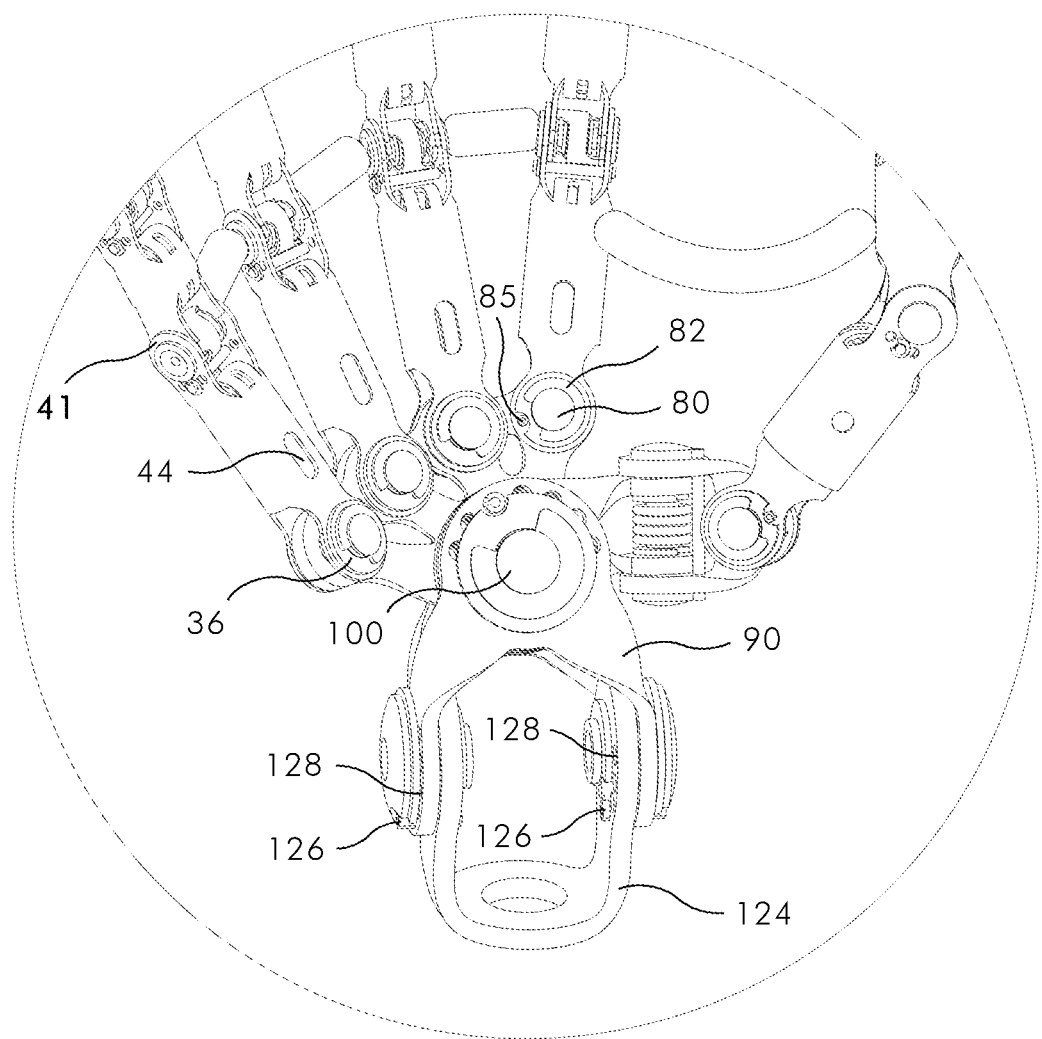
FIG. 16 is front perspective view of the installed prosthetic hand finger locking assembly.

The finger digit's metacarpals 24 and the thumb digit's axially adjustable metacarpal 26 have a similar but slightly different structure than the phalanges, although still based on the tube section design. In FIG. 16 it can be seen that the tube section still retains the two parallel coupling flanges 41 at its distal end, however at the proximal end, there are two parallel palm flanges 36. The plane of the palm flanges 36 on the finger assemblies or digits reside perpendicular to the plane of the coupling flanges 41 and there are no cable guides 42 at the proximal end. Rather, there are cable slots 44 on the palmer and dorsal sides of the metacarpus 24 to allow passage of cables. The coupling flanges 41 and palm flanges 36 are substantially similar but for their orientation on the tube section. The palm flanges 36 also have centrally located pivot pin orifices 40 formed therethrough.

Figure 3:
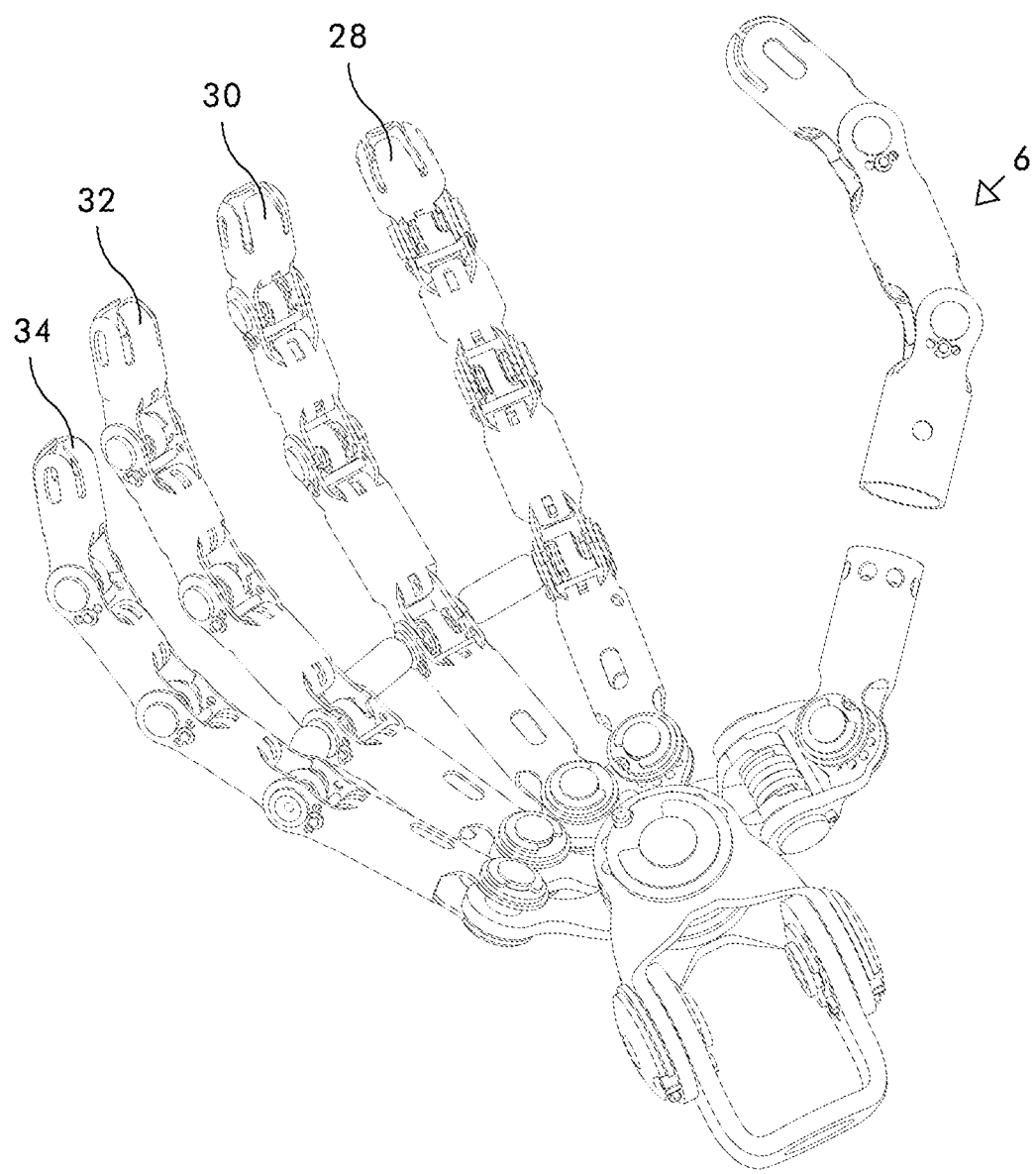
FIG. 3 is a front perspective view of the prosthetic hand with an exploded thumb.

The thumb digit metacarpal's structure as shown in FIGS. 3 and 4, is slightly different to allow for the thumb digit 6 to axially adjust. In this manner it may oppositionally contact any desired finger digit. The thumb digit 6, when straightened, has a linear axis that it is rotatable about so as to enable adjustable angle opposable contact with at least one of the finger digits. To accomplish this, the thumb digit 6 has a two piece tube construction rather than a single tube section 38. It resembles finger digit metacarpals that have been axially cut. The distal half of this metacarpal 26 has a pair of opposing adjustment orifices 56 formed therethrough. The proximal half of this metacarpal 26 has a series of radially drilled orifices 58 therethrough. The proximal half has an outer diameter sized for frictional but sliding rotation within the slightly larger inner diameter of the distal end 46. When assembled, two of the radially drilled orifices 58 will align with the two adjustment orifices 56 for the insertion of a mechanical fastener. This allows the fixable, axial adjustment of the thumb digit 6. Although in alternate embodiments, other rotational locking devices may be utilized. There may or may not be finger assemblies that resemble thumb digits in the mechanical grasping device.

Figure 11:
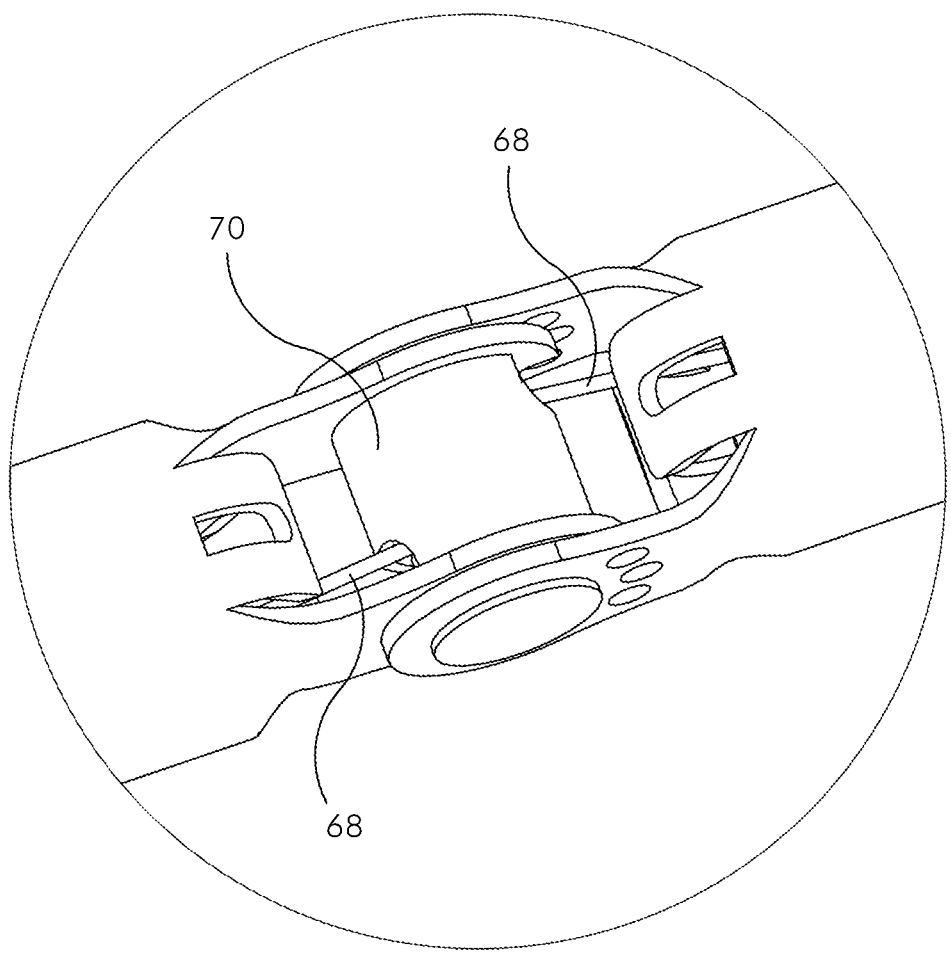
FIG. 11 is a close up top perspective view of two connected phalanges tubes.
Figure 12:
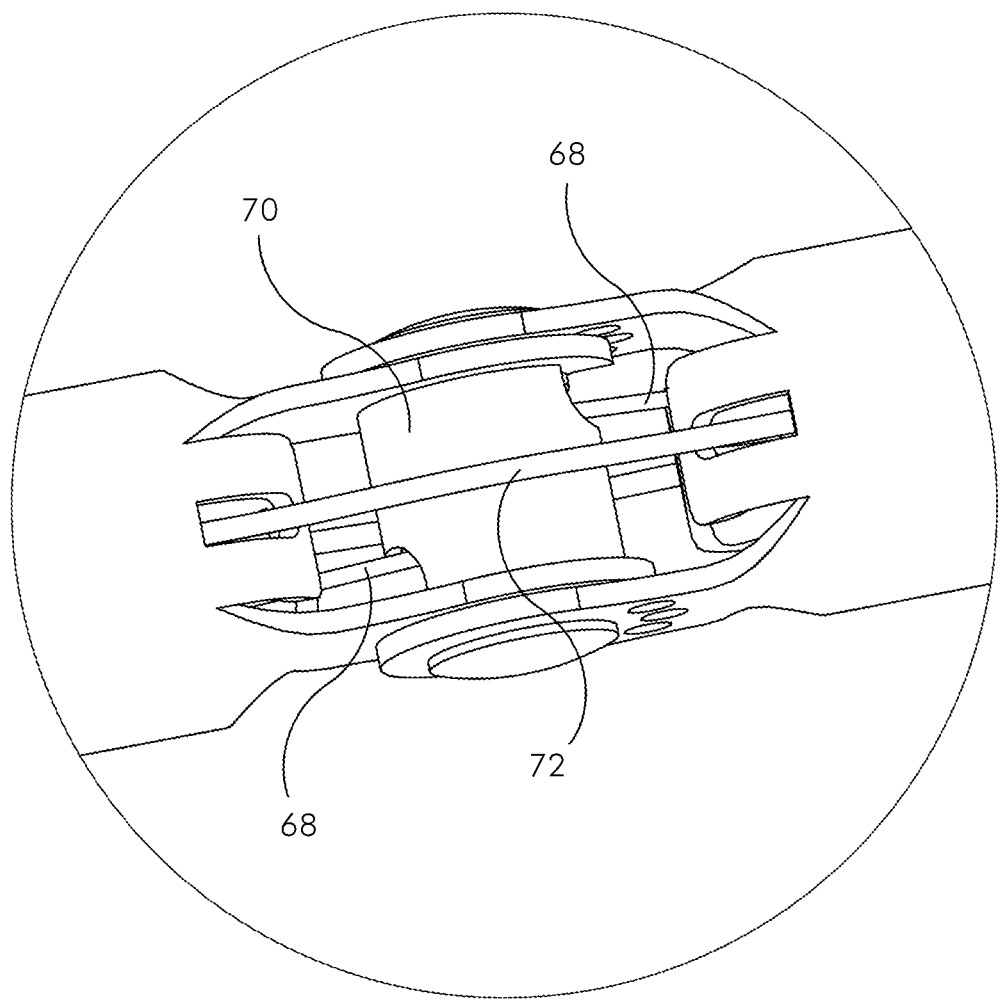
FIG. 12 is a close up top view of two connected phalanges tubes.

The tube sections digits are assembled in the following fashion to make finger digits. (In the case of the mechanical prosthetic hand. the digit segments are connected to make a finger assembly in the following fashion.) The proximal end of the distal phalange 18 is connected to the distal end of the middle phalange 20, and the proximal end of the middle phalange 20 is connected to the distal end of the proximal phalange 22, and the proximal end of the proximal phalange is connected to the distal end of metacarpal 24 or 26 in the identical manner outlined above to facilitate the linear assembly of the digits (finger 4 or thumb 6). In the case of the thumb digit 6, the middle phalange 20 is eliminated and the distal phalange's proximal end is connected to the distal end of the proximal phalange 22. The assembly of the individual phalange-phalange connections, and phalange-metacarpal connections of the finger digits and thumb digit, are best explained in FIGS. 10-12 with reference to the connection between a distal phalange 18 and a middle phalange 20. It is to be noted that each of the digits (and thus the entire hand) are scalable because each of the individual phalanges are available in differing lengths and each digit may be made of a customized array of different sized phalanges.

Beginning with a distal phalange 18, the two coupling flanges 41 at the proximal end 48 of the tube section are fitted adjacent (on top or below) of the two coupling flanges 41 at the distal end 46 of the middle phalange 20 such that their pivot pin orifices 40 align. Through one set of aligned pivot pin orifices 40 is inserted a first pivot pin 60. The pivot pin 60 is less than one half of the width distance between the parallel connection flanges 41 of a tube section 38. Each pivot pin 60 has a head that resides normally to a shaft section that has an axial groove 64 formed therein, sized to accept a circular retaining clip 62. These are commercially available mechanical fasteners, well known in the art. A retaining clip 62 is placed in the axial groove 64 in the pivot pin 60 such that the inner face of the retaining clip 62 resides adjacent to the inner face of the distal end 46 of the middle phalange 20. A torsion (wound) spring 66 is placed over the shaft section of the pivot pin such that its two spring legs 68 (that reside 180 degrees apart and at opposite ends of the spring body) are constrained by the inner wall of the tube sections 38 of the connected phalanges and or metacarpals. (These spring legs 68 are long enough to extend into the internal cavity of the tube section 38.) A spring cover 70 is placed over the spring 66 and the underlying shaft section of the first pivot pin shaft section, and a second pivot pin 60 is installed and affixed through the second set of aligned pivot pin orifices 40 in the distal phalange's proximal end 48 and the middle phalange's distal end 46 in an identical fashion as described above. The spring cover 70 merely prevents the cable 72 from interfering with the spring 66. It is to be noted that the spring 66 may be oriented such that the torsional spring legs 68 may either open or close the joint. The closing order of individual phalanges is determined by the strength of the respective wound springs selected for use in that specific phalange. Generally the strength of each wound spring decreases toward the distal end of the finger assemblies.

Figure 10:
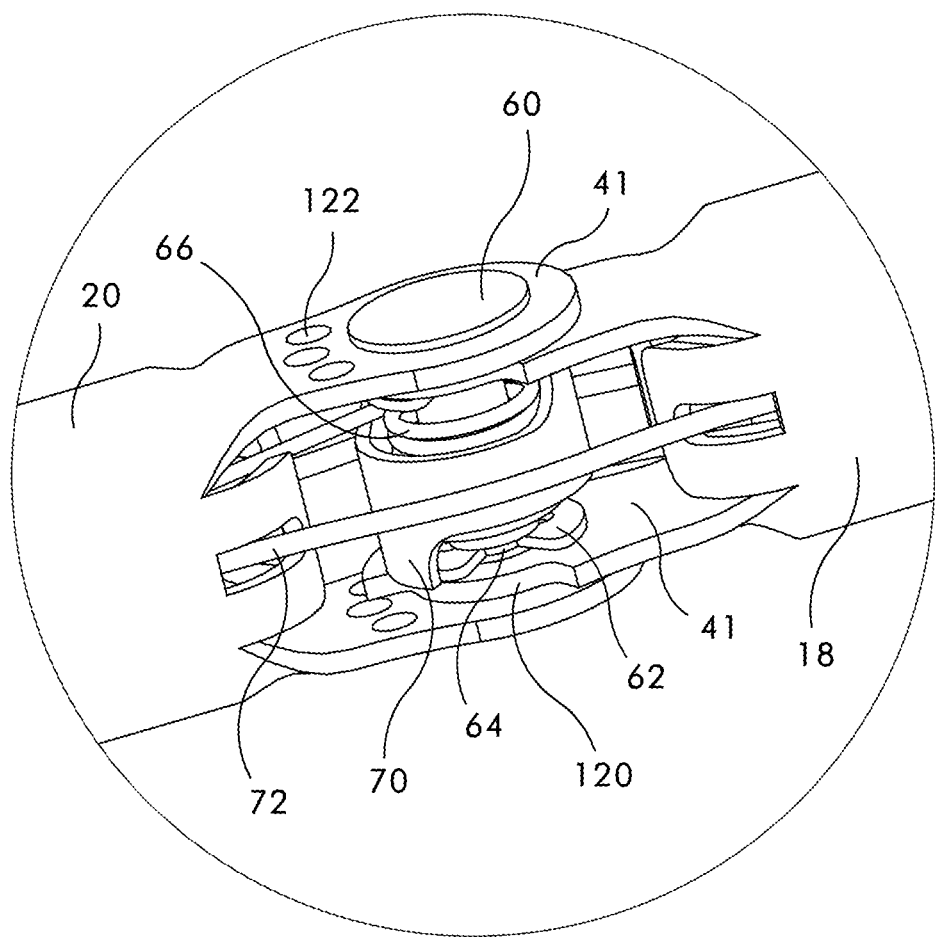
FIG. 10 is a close up bottom perspective view of two connected phalanges tubes.

Looking at FIGS. 8, 9 and 10, there is peripheral detent section 120 cut in the perimeter of the coupling flanges 41 on the proximal end of the phalanges. These act in conjunction with an adjustable stop pin (removed for visual clarity) that is installed in one of a series of stop pin orifices 122 formed there through the distal ends of the coupling flanges 41 of the metacarpals and phalanges. This system of stop pins and detents allows for control of the range of motion of the joints and serve as backstops (e.g. to prevent hyperextension.)

The remaining connections of the phalanges and metacarpals of digits 4 and 6 are similarly made. The cable 72 is routed through cable guides 42 traversing the linear arrangement of phalanges and metacarpals, passing through the internal cavity of each tube section 38 and the consecutive cable slots 44. The distal end of cable 72 is affixed to the distal end of each distal phalange 18.

It is to be noted that the cable system used to operate the digits may be of two different configurations. The first configuration (preferred embodiment) uses two cables 72, one internally traversing the dorsal side and one individually traversing the palmar side of the digit, each running over the palmar plate 8 and operably connected at its proximal end to the user's preferred control system. (e.g. body-powered or myoelectric) The second configuration utilizes but one cable routed through either the palmer or dorsal side of the digits and similarly operationally connected as above. Where only one cable 72 is provided, the springs 66 serve to return the digits to the open or closed position depending on whether the cable runs on the palmar side and closes the digit or the dorsal side and opens the digit. (In this way the hand 2 can be configured to operate in either the voluntary-open or voluntary-closed modes.)

The stiffness of the springs 66 are set for differing tensions across the various phalanges (each phalange relative to the adjacent phalange) so as to control the closing profile of the entire hand similar to that of the human form or as desired. Generally, the spring 66 is set to open (extend) the finger at the joints with the weakest spring tension (stiffness) at the distal end of the middle phalange and increasing gradually toward the proximal end of the proximal phalange.

Looking at a voluntary-close configuration, the cable 72 on the palmar side of the digits under tension actively draw the digits inward in flexion. Since each joint is held extended by differing spring tensions, when the cable 72 is tensioned, the digits curl inward first from the distal end in a humanlike fashion where the joints with the weaker spring forces begin to curl inward first. All joints passively spring open when the palmar cable tension is relieved.

If a single-cable, voluntary-open (cable tension to open) system is employed, the cable on the dorsal side of the digits under tension draw the digits outward in extension and the springs 66 serve to close the digits in flexion.

If a single cable voluntary-close (cable tension to close) system is employed, the cable on the palmar side of the digits under tension draw the digits inward in flexion and the springs 66 serve to extend the digits.

In a dual cable system, the tension of either cable actively controls both the flexion or extension of the digits. Wherein there is no or reduced dorsal cable tension, the springs 66 again act to control either the opening or closing profile of the digits.

Figure 13:
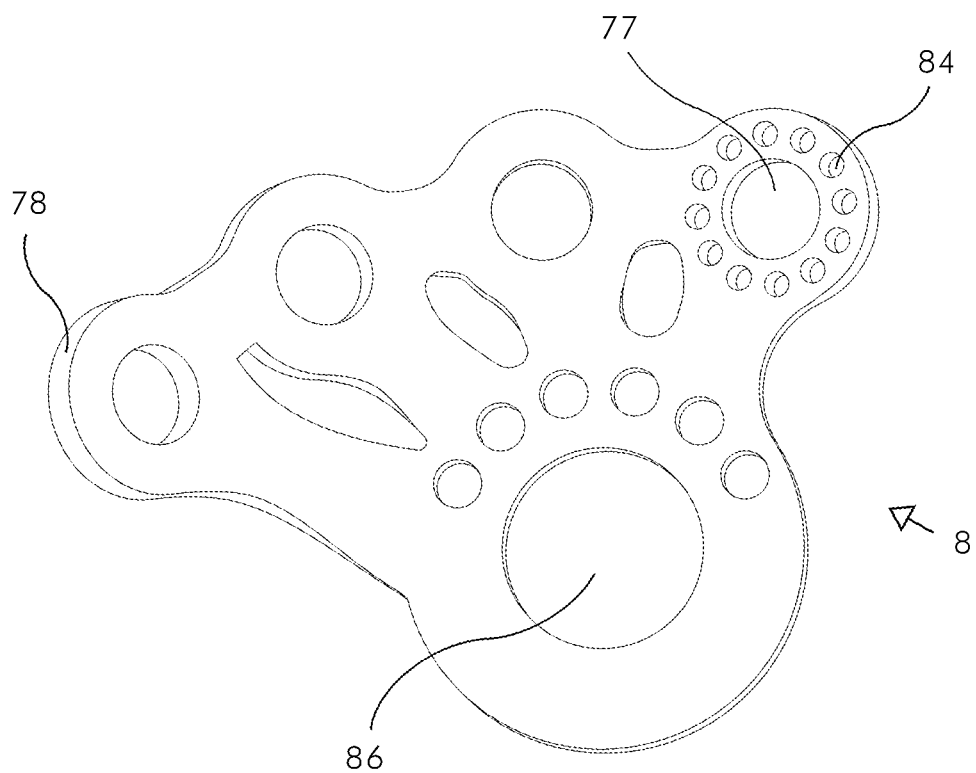
FIG. 13 is a front perspective view of the palmer plate.

FIG. 13 illustrates the means for operationally supporting all of the digits or digital movements (called the support member or palmar plate 8). This is a curved plate that acts as the anchor point for the proximal end of the finger digit metacarpals 24 (directly) (or finger assemblies) and the thumb digit metacarpal 26 (indirectly) as well as the connector to the wrist 16. The palmar plate 8 (support member) has a series of metacarpal orifices 77 (preferably four in number) formed therethrough that lie in a row adjacent the top perimeter edge 78. Looking at FIG. 16, it can be seen that these metacarpal orifices 77 accommodate the connection of the finger digits by alignment with the pivot pin orifices 40 in the palm flanges 36 so that a pin 80 with a groove to retain circlip (ore-clip) 82 may be inserted into the aligned orifices. It is known that other mechanical connectors could be optionally used here. Optionally, there may be a flexible, slightly compressible polymer disc (plain bearing) placed between either or both of the palm flanges 36 and the palmar plate 8 to aid and silence pivotal movement of the metacarpals, as well as increase the overall digit flexibility or deflection. In this manner of connection, and with the flexible spacers 14, the four finger digits (finger assemblies) can be pivoted as a group on the palmar plate 8 (support member). The index metacarpal orifice 77 has a series of lock orifices 84 arranged radially about it on the palmer plate 8. These allow the temporary locking of the index digit in a specific position and relative to the thumb digit 6 and the palmar plate 8 to accomplish a mechanical endeavor. This positioning is accomplished with a mechanical member 85 (or in the case of the mechanical grasping device, a lock means.) that passes through one of the lock orifices 84 and an orifice 202 in the palmer flange 36 of the index digit metacarpal 24. (Visible in FIG. 17.)

Figure 14:
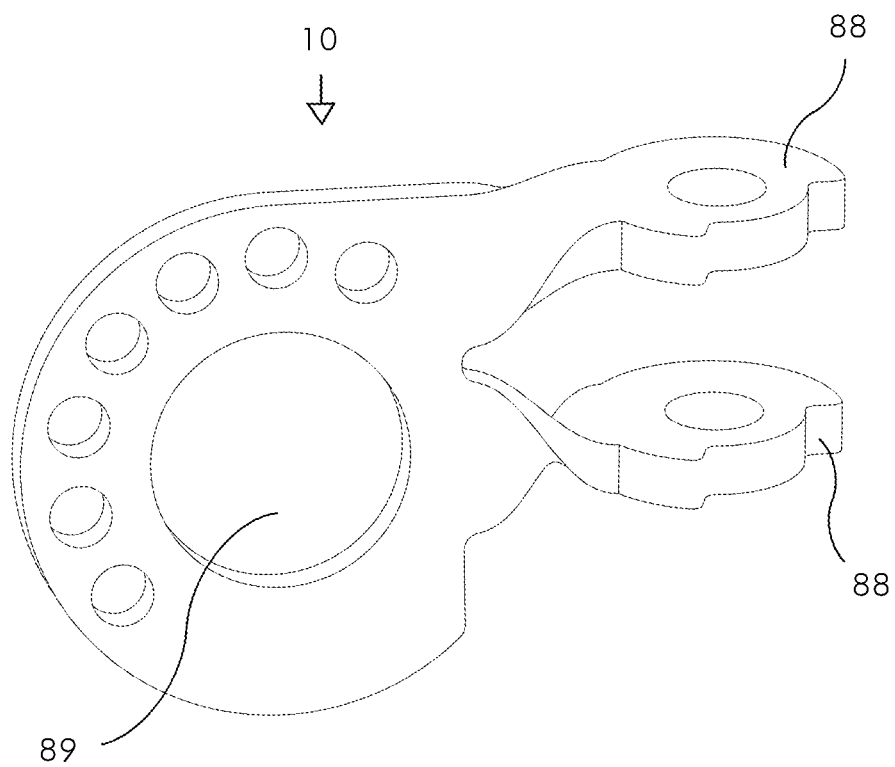
FIG. 14 is front perspective view of the thumb pivot flange.
Figure 15:
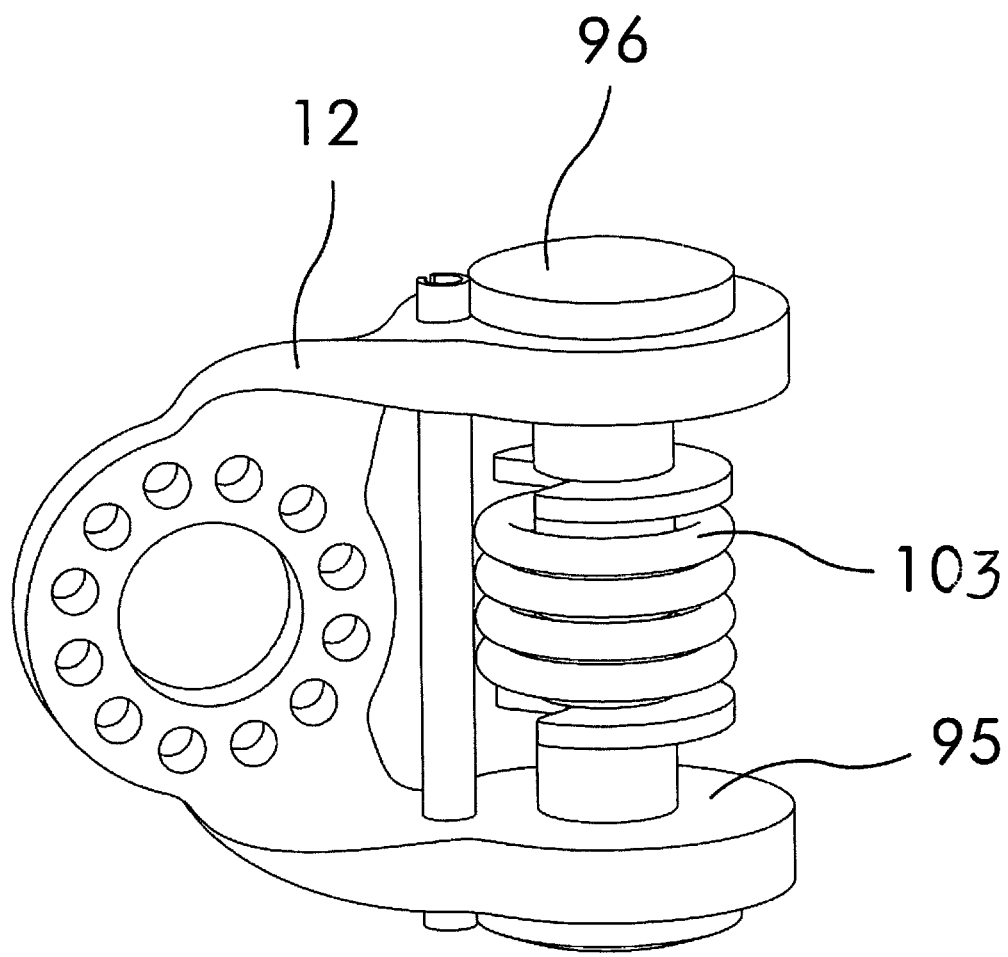
FIG. 15 is a front perspective view of the thumb rotation plate.

On the palmar plate 8 there is also a central orifice 86 that allows the connection of the wrist top bracket 90 and the thumb rotation plate 10. The thumb rotation plate 10 (FIG. 14) with a central opening 89 and a pair of parallel hinge arms 88 that extend therefrom. The thumb rotation plate 10 is affixed to the central region of the palmar plate 8 by alignment of its central opening 89 with the palmer plate's central orifice 86 below, both sandwiched between the wrist's top bracket 90. The wrist's top bracket 90 has an orifice that when aligned with the central opening 89 will accept the insertion of mechanical fastener 101 therethrough. In this manner the thumb rotation plate 10, the palmer plate 8 and the wrist top bracket 90 may all pivot relative to each other. This mechanical pinning with fastener 101 is similar to that used to lock the index digit 28 and the thumb digit 6.

Between the parallel hinge arms 88 of the thumb rotation plate 10 is pivotally affixed the thumb pivot flange 12. This pivot flange 12 has a pair of parallel ears 95 that are substantially similar to the hinge arms 88. The ears 95 are located atop each of the hinge arms 88 and at least one thumb pivot pin 96 inserted therethrough. This may be accomplished in a fashion similar to that of the digit joints as outlined herein.

There is a torsion coil spring 103 around the thumb pivot pin 96 that functions to apply rotational torque between the thumb rotation plate 10 and the thumb pivot flange 12 so as to keep the thumb digit 6 in an open position relative to the palmer plate 8. This ensures that as the user approaches an object to manipulate, the thumb is not initially in the way of the operation. This gives a maximally open position for grasping.

The wrist top bracket 90 (FIGS. 4 and 16) is matingly engaged for adjustable lockable pivotal positioning with the wrist bottom bracket 124. Again this uses a mechanical fastener 126 passing through a series of aligned orifices 128 in these wrist components similar to the system employed with the index digit. The bottom wrist bracket 124 may be affixed to the rest of the prosthesis in a plethora of ways commonly known in the field. It accommodates the passage of the cables 72 to their intended control points.

The mechanical hand as disclosed herein, has been discussed in association with uses as a prosthetic hand although use in the robotics industry is anticipated that it may be a simplified embodiment specializing in grasping items (the mechanical grasping device) with a series of operable servo motors controlling the various digits. It is envisioned that the control of the individual digits through the servo motors may be manipulated by a device affixed to the hand of the operator so as to mirror their digit movements.

Figure 22:
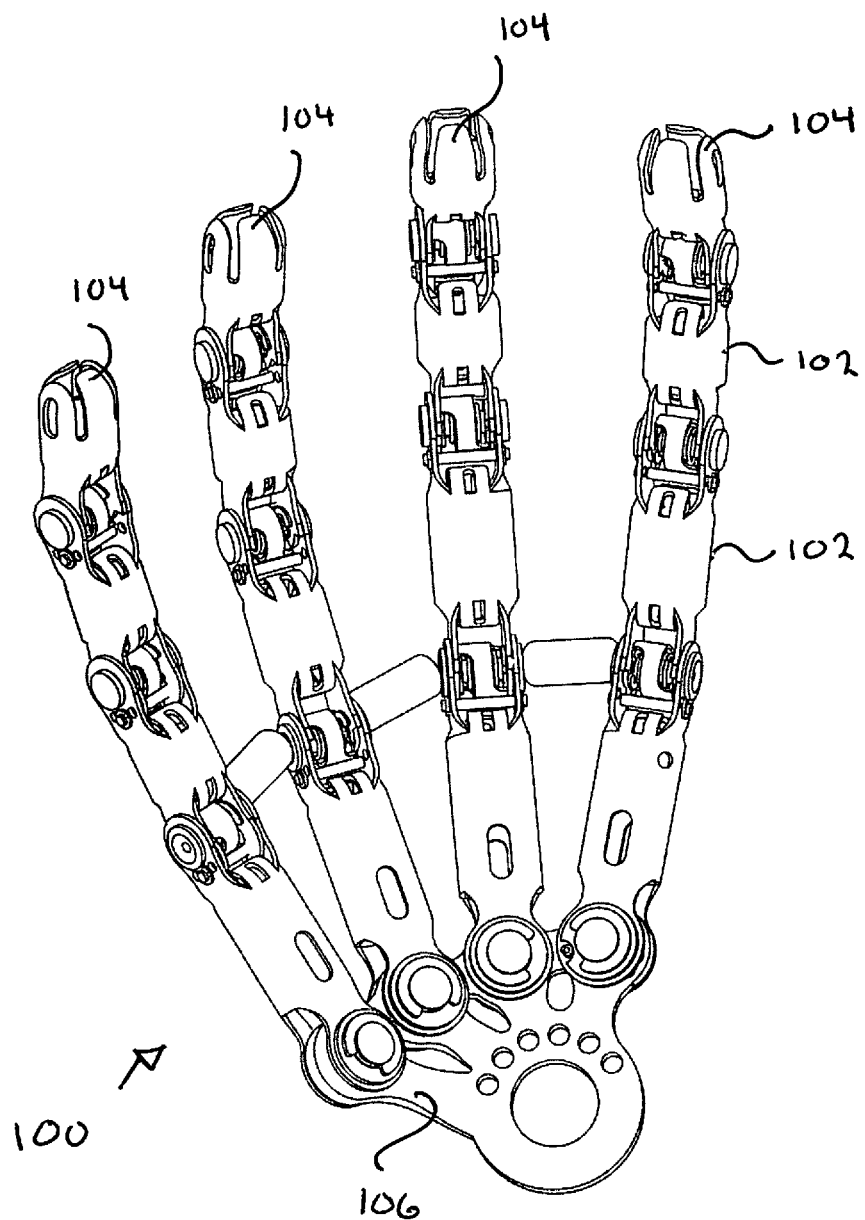
FIG. 22 is a front perspective view of the mechanical grasping device embodiment.

FIG. 22 illustrates a mechanical grasping device 100 with four multi digit section finger assemblies 104 pivotally connected to a support member 106. Here, it can be seen that the proximal end of the finger assemblies pivot in a plane substantially perpendicular to the plane of the hinged finger curl. The digit segments 102 at the proximal end of the finger assemblies have their connection to the support member oriented 90 degrees from their connection to other digital segments.

The mechanical hand 2 is a complex variation of the mechanical grasping device 100 that involves a thumb and finger assemblies with four finger digits. The mechanical grasping device 100 is a striped down embodiment of the mechanical hand 2 that has a minimum of the repeated structural elements of the mechanical hand 2. The mechanical grasping device 100 need only have two finger assemblies each with but two hingeable digit segments 102 affixed for joint pivotal motion by palm flanges at their proximal ends on the support member 106 to which they are pivotally affixed. Through this design, each finger assembly and its digit segments 102 are moveable in a first plane in a finger assembly hinged curl. All of these first planes are approximately parallel. Each finger assembly's pivotally connection to the support member allows the finger assembly to pivot in a second plane that is approximately perpendicular to the first plane (plus or minus 20 degrees). All of these second planes are approximately parallel. Between each finger assembly is a flexible spacer 14 along the width of the mechanical grasping device 100 that allows for the crushabilty feature described herein with respect to the mechanical hand.

It is to be noted that the finger assemblies are independently capable of forming their curled configuration in the first plane independently of the pivotally motion of the finger assemblies on the support member. Also the finger assemblies reside at a variable distance from each other which can be adjusted by manipulation of the flexible spacer affixed between adjacent finger assemblies.

From the disclosure it can be seen that the present invention prosthetic hand has a plethora of capabilities not previously provided in the prior art prosthetic hands. It is both scalable and scalable proportionately because each of the segments of the digits, the palmar plate, the thumb pivot plate and the wrist are individually sizeable, likewise all components of the prosthetic hand distal of the wrist are similarly scalable. This allows for individual customization of geometric configurations tailored to specific use patterns (eg., longer fingers wherever needed.) The prosthetic hand can be powered by the body (manual) or a motive source (electricity, hydraulics etc) under myoelectric signal operation. The hand is crushable since it is capable of having flexible and pivotable connections between rigid members along the length and width of the hand. It is waterproof having a lack of sensitive electronics. It has a strong lightweight design due to the hollow tubular member design. It is modular wherein individual parts can be replaced for quick repair. It can perform multiple tasks because of its individually adjustable, controlable finger digits. From an aesthetics point, it is visually pleasing able to be offered in colors and textured gripable soft resilient digit sleeves. The hand can be operated in the voluntary-open or voluntary-closed position by simply installing the springs in the digits in a reverse manner. It will deform before failing thereby giving indication of overload before failure. Its body powered version will be "plug and play" into the existing prior art sockets allowing patients to have the option of switching out prosthetic hands and not having to relearn how to work their cable harness again. It offers excellent visibility of objects grasped due to the separation of finger digits and the voided areas of the palm and digits. Finally, the hollow digit structure allows for ample room to add future internal components from emerging technology.

Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Having thus described the invention, what is claimed as new and desired to be secured by Letters Patent is as follows:

1. A mechanical grasping device comprising:
    a support member;
    a lockble first finger assembly made of a first middle phalange hingedly connected to a first proximal phalange, said first proximal phalange hingedly connected to a crushable palm formed in part by a first metacarpal, said first metacarpal pivotally and directly connected to said support member so as to enable a crushable motion of said crushable palm;
    wherein said first middle phalange and said first proximal phalange are curlable in a first plane, and said first finger assembly is pivotable in a third plane;
    a second finger assembly made of a second middle phalange hingedly connected to a second proximal phalange, said second proximal phalange hingedly connected to a second metacarpal forming a second part of said crushable palm, said second metacarpal pivotally connected to said support member so as to enable said crushable motion of said crushable palm;
    wherein said second middle phalange and said second proximal phalange are curlable in a second plane, and said second finger assembly is pivotable in said third plane;
    a radial series of lock orifices formed through said first metacarpal;
    a support member orifice formed through said support member;
    a lock means insertable between said radial series of lock orifices and said support member orifice to lock said first finger assembly to said support member and prevent pivotal motion of said first finger assembly in said third plane; and
    wherein said first plane is parallel to said second plane and said first and second planes are perpendicular to said third plane.

2. The mechanical grasping device of claim 1 further comprising:
    a flexible spacer disposed between said first metacarpal and said second metacarpal, said flexible spacer limiting distance there between said first metacarpal and said second metacarpal.

3. The mechanical grasping device of claim 2 further comprising:
    four springs;
    wherein a first spring of said four springs is connected to said first middle phalange and said first proximal phalange, a second spring of said four springs is connected to said first proximal phalange and said first metacarpal, a third spring of said four springs is connected to said second middle phalange and said second proximal phalange, and a fourth spring of said four springs is connected to said second proximal phalange and said second metacarpal; and wherein said first spring has a first tension force that is less than a second tension force of said second spring, and said third spring has a third tension force that is less than a fourth tension force of said fourth spring.

4. The mechanical grasping device of claim 3 further comprising:

four torsional springs each having a wound spring body with two spring legs that extend 180 degrees apart from opposite ends of said wound spring body;

four pivot pins;

wherein a first of said four pivot pins connects said first middle phalange and said first proximal phalange, a second of said four pivot pins connects said first proximal phalange to said first metacarpal, a third of said four pivot pins connects said second middle phalange and said second proximal phalange, and a fourth of said four pivot pins connects said second proximal phalange to said second metacarpal;

wherein each of said four torsional springs has one of said four pivot pins passing through said wound spring body.

5. The mechanical grasping device of claim 2 wherein said flexible spacer lies in a plane parallel to said third plane.

6. The mechanical grasping device of claim 1 further comprising:

four springs;

wherein a first spring of said four springs is connected to said first middle phalange and said first proximal phalange, a second spring of said four springs is connected to said first proximal phalange and said first metacarpal, a third spring of said four springs is connected to said second middle phalange and said second proximal phalange, and a fourth spring of said four springs is connected to said second proximal phalange and said second metacarpal; and wherein said first spring has a first tension force that is less than a second tension force of said second spring, and said third spring has a third tension force that is less than a fourth tension force of said fourth spring.

7. The mechanical grasping device of claim 6 further comprising:

four pivot pins; and wherein said four springs are torsional springs each having a wound spring body with two spring legs that extend 180 degrees apart from opposite ends of said wound spring body;

wherein a first pivot pin of said four pivot pins connects said first middle phalange and said first proximal phalange, a second pivot pin of said four pivot pins connects said first proximal phalange to said first metacarpal, a third pivot pin of said four pivot pins connects said second middle phalange and said second proximal phalange, and a fourth of said four pivot pins connects said second proximal phalange to said second metacarpal;

wherein each of said four torsional springs has one of said four pivot pins passing through said wound spring body.

8. The mechanical grasping device of claim 1:

wherein said first middle phalange has a first size that is different from a second size of said first proximal phalange, and wherein said second middle phalange has a third size that is different from a fourth size of said second proximal phalange.

* * * * *